(12) United States Patent
Norel et al.

(10) Patent No.: US 12,417,828 B2
(45) Date of Patent: Sep. 16, 2025

(54) EXPERT CROWDSOURCING FOR HEALTH ASSESSMENT LEARNING FROM SPEECH IN THE DIGITAL HEALTHCARE ERA

(71) Applicant: International Business Machines Corporation, Armonk, NY (US)

(72) Inventors: Raquel Norel, New York, NY (US); Guillermo Cecchi, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 105 days.

(21) Appl. No.: 18/325,244

(22) Filed: May 30, 2023

(65) Prior Publication Data

US 2024/0404667 A1    Dec. 5, 2024

(51) Int. Cl.
  *G16H 15/00*    (2018.01)
  *G10L 15/26*    (2006.01)
  *G16H 10/20*    (2018.01)

(52) U.S. Cl.
  CPC ........... *G16H 15/00* (2018.01); *G10L 15/26* (2013.01); *G16H 10/20* (2018.01)

(58) Field of Classification Search
  CPC ........ G16H 10/20; G16H 10/60; G16H 15/00; G16H 40/20; G16H 50/20; G16H 50/30; G16H 50/70; G16H 80/00
  See application file for complete search history.

(56) References Cited

U.S. PATENT DOCUMENTS

| | | |
|---|---|---|
| 8,805,756 B2 | 8/2014 | Boss et al. |
| 9,424,354 B2 | 8/2016 | Teevan et al. |
| 10,650,916 B2 | 5/2020 | Moturu et al. |
| 10,748,644 B2 | 8/2020 | Shriberg et al. |

(Continued)

FOREIGN PATENT DOCUMENTS

| WO | WO-2021235866 A1 | * 11/2021 | ............. G06N 3/084 |
|---|---|---|---|
| WO | WO-2023219896 A1 | * 11/2023 | ......... G06F 16/2457 |

OTHER PUBLICATIONS

Gross et al., Working together? Teamwork in treating diabetes and hypertension in Israeli managed care organizations, Mar. 8, 2008, International Journal of Health Care Quality Assurance, vol. 22, No. 4, pp. 353-365. (Year: 2008).*

(Continued)

*Primary Examiner* — Christopher L Gilligan
(74) *Attorney, Agent, or Firm* — Yee & Associates, P.C.

(57) ABSTRACT

Objective health assessment is provided. An utterance of a patient is received in response to a question being presented to the patient. A transcription is generated of the utterance. A set of sentence embeddings is generated from the transcription of the utterance. A plurality of sentence embeddings corresponding to characteristics of a health condition is retrieved. Similarity is measured between the set of sentence embeddings generated from the transcription of the utterance and the plurality of sentence embeddings corresponding to the characteristics of the health condition. A result of a health assessment of the patient is sent to a healthcare professional based on the similarity between the set of sentence embeddings generated from the transcription of the utterance and the plurality of sentence embeddings corresponding to the characteristics of the health condition.

20 Claims, 5 Drawing Sheets

(56) References Cited

U.S. PATENT DOCUMENTS

| | | | |
|---|---|---|---|
| 10,835,167 B2 | 11/2020 | Voss et al. | |
| 2006/0100880 A1* | 5/2006 | Yamamoto | G16H 50/30 |
| | | | 704/270 |
| 2013/0132308 A1 | 5/2013 | Boss et al. | |
| 2018/0197439 A1* | 7/2018 | Gordon | G09B 19/04 |
| 2018/0285528 A1 | 10/2018 | Healey et al. | |
| 2018/0296092 A1* | 10/2018 | Hassan | G16H 50/20 |
| 2019/0019581 A1 | 1/2019 | Vaughan et al. | |
| 2019/0385711 A1 | 12/2019 | Shriberg et al. | |
| 2021/0058513 A1* | 2/2021 | McNeil | G06F 40/295 |
| 2021/0233623 A1 | 7/2021 | Harper et al. | |
| 2022/0166730 A1* | 5/2022 | Bastide | H04L 65/80 |
| 2022/0189486 A1* | 6/2022 | Yim | G06F 40/279 |
| 2022/0375622 A1* | 11/2022 | Gnanasambandam | |
| | | | G16H 15/00 |
| 2023/0317274 A1* | 10/2023 | Alam | G06F 40/40 |
| | | | 705/2 |

OTHER PUBLICATIONS

Celi et al., "Crowdsourcing Knowledge Discovery and Innovations in Medicine," Journal of Medical Internet Research (JMIR), vol. 16, No. 9, Sep. 19, 2014, 5 pages. https://www.jmir.org/2014/9/e216/?trendmd-shared=0CachedSep.

Crequit et al., "Mapping of Crowdsourcing in Health: Systematic Review," Journal of Medical Internet Research (JMIR), vol. 20, No. 5, May 15, 2018, 23 pages. https://www.jmir.org/2018/5/e187/.

Grace Period Disclosure: Chan et al., "Emergence of Language Related to Self-experience and Agency in Autobiographical Narratives of Individuals With Schizophrenia," Schizophrenia Bulletin, vol. 49, Issue 2, Mar. 2023, published Oct. 3, 2022, 10 pages. https://academic.oup.com/schizophreniabulletin/article/49/2/444/6731748.

* cited by examiner

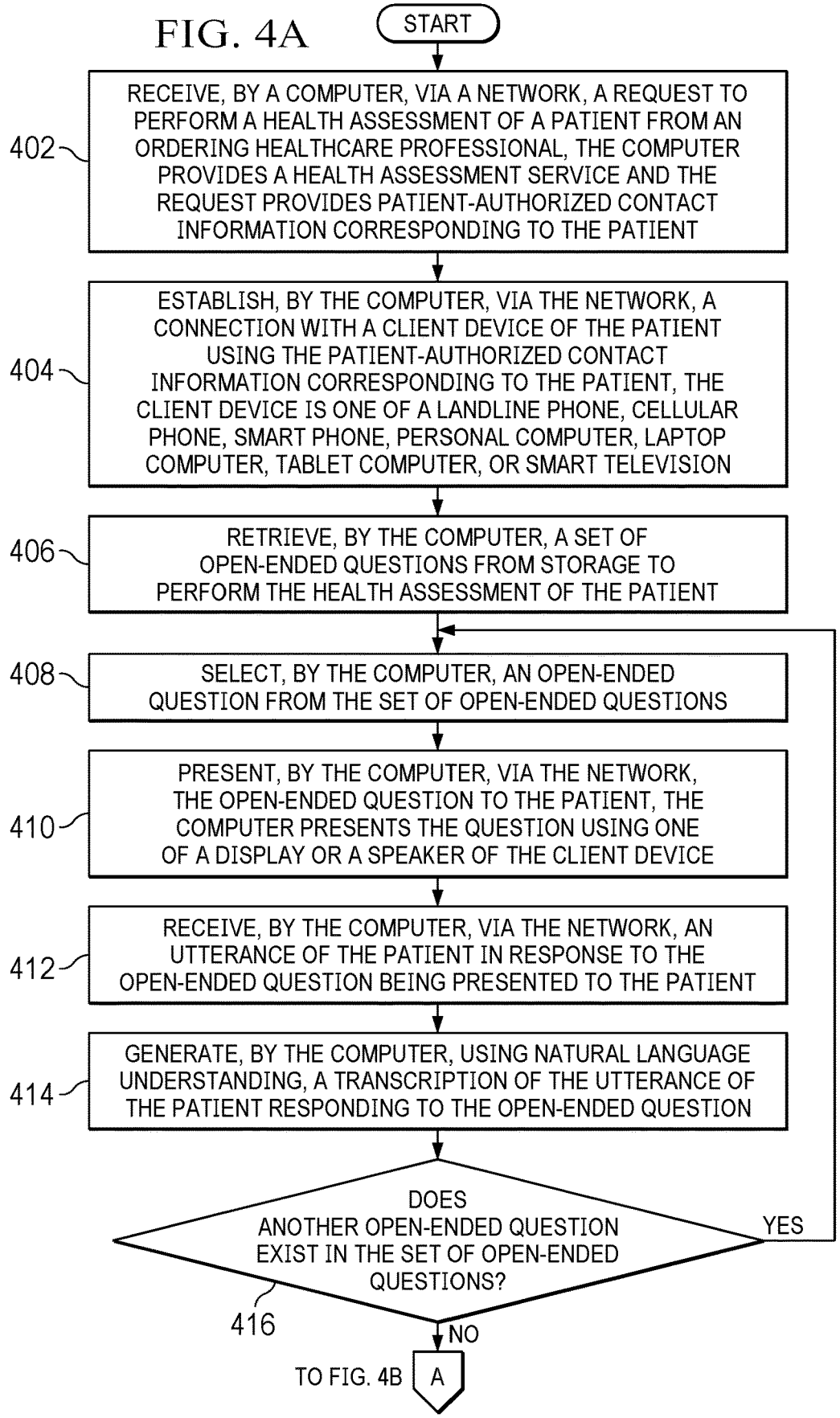

EXPERT CROWDSOURCING FOR HEALTH ASSESSMENT LEARNING FROM SPEECH IN THE DIGITAL HEALTHCARE ERA

BACKGROUND

The disclosure relates generally to healthcare and more specifically to objective health assessment.

Adverse health conditions can result in a combination of symptoms that interfere with a person's activities of daily living (e.g., working, sleeping, eating, socializing, and the like). Changes in a person's health can be triggered by or attributed to one or multiple factors such as emotional distress, job stress, poor diet, lack of sleep, lack of exercise, substance abuse, and the like. Current methods of detecting health conditions in individuals are limited, which can cause health conditions to remain undiagnosed and untreated. For example, it is unrealistic to expect clinicians to conduct queries of clinical data to generate evidence or data-driven decisions for each patient.

SUMMARY

According to one illustrative embodiment, a computer-implemented method for objective health assessment is provided. A computer receives an utterance of a patient in response to a question being presented to the patient. The computer generates a transcription of the utterance of the patient responding to the question. The computer generates a set of sentence embeddings from the transcription of the utterance made by the patient. The computer retrieves a plurality of sentence embeddings corresponding to characteristics of a health condition. The computer measures similarity between the set of sentence embeddings generated from the transcription of the utterance made by the patient and the plurality of sentence embeddings corresponding to the characteristics of the health condition. The computer sends a result of a health assessment of the patient to a healthcare professional based on the similarity between the set of sentence embeddings generated from the transcription of the utterance made by the patient and the plurality of sentence embeddings corresponding to the characteristics of the health condition. According to other illustrative embodiments, a computer system and computer program product for objective health assessment are provided.

BRIEF DESCRIPTION OF THE DRAWINGS

FIGS. 4A-4B are a flowchart illustrating a process for objectively assessing patient health in accordance with an illustrative embodiment.

DETAILED DESCRIPTION

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc), or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Figure 1:
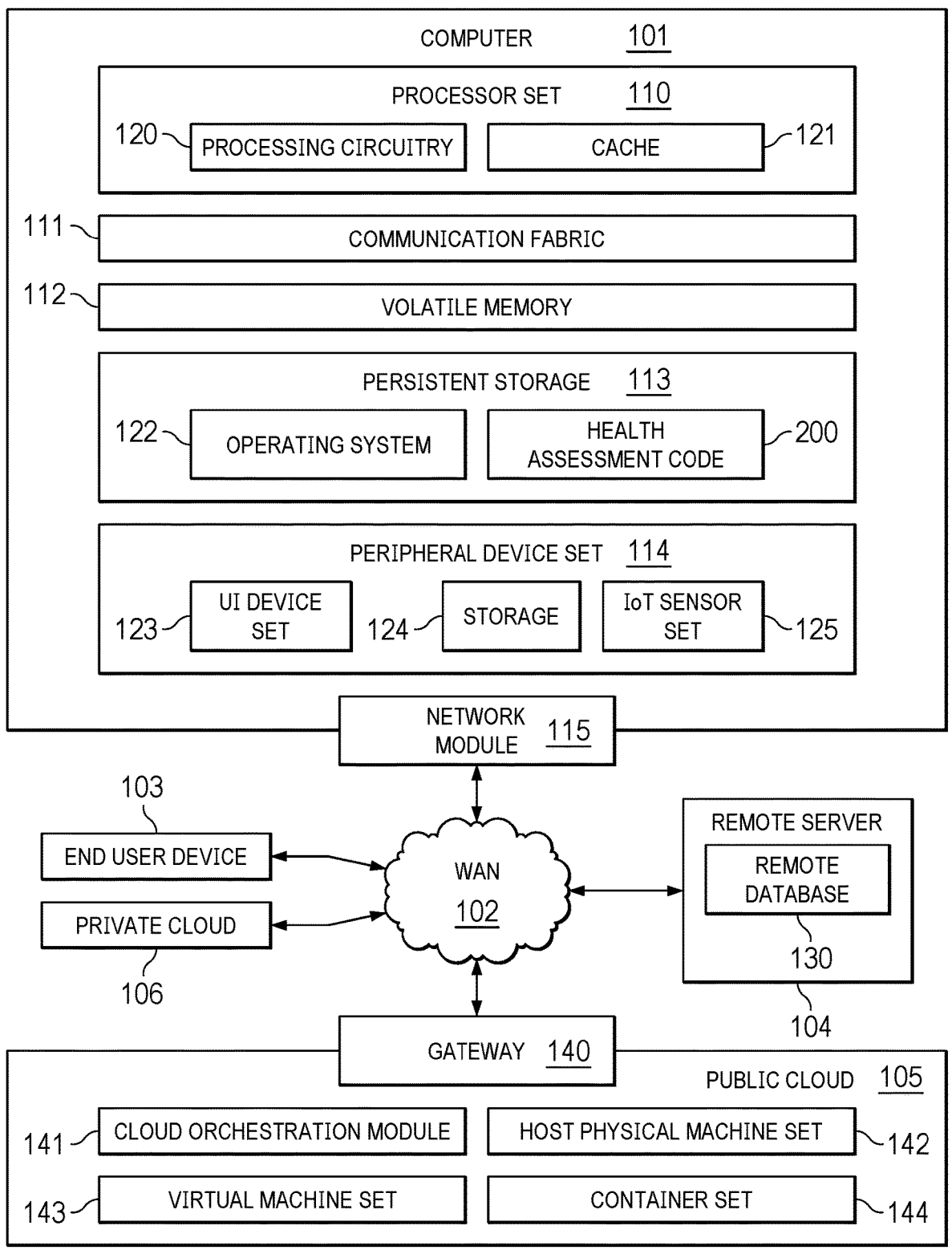
FIG. 1 is a pictorial representation of a computing environment in which illustrative embodiments may be implemented.
Figure 2:
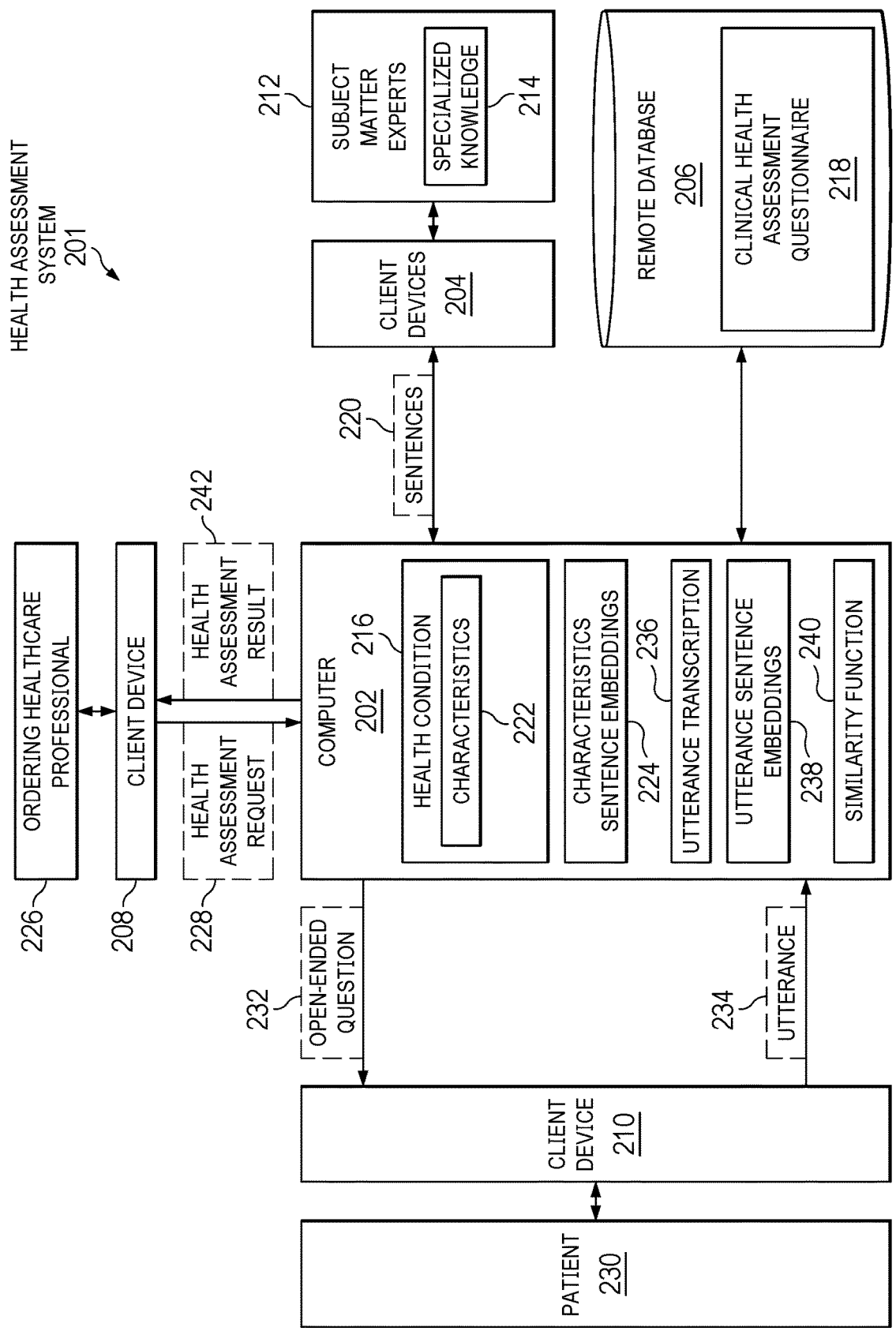
FIG. 2 is a diagram illustrating an example of a health assessment system in accordance with an illustrative embodiment.

With reference now to the figures, and in particular, with reference to FIGS. 1-2, diagrams of data processing environments are provided in which illustrative embodiments may be implemented. It should be appreciated that FIGS. 1-2 are only meant as examples and are not intended to assert or imply any limitation with regard to the environments in which different embodiments may be implemented. Many modifications to the depicted environments may be made.

FIG. 1 shows a pictorial representation of a computing environment in which illustrative embodiments may be implemented. Computing environment 100 contains an example of an environment for the execution of at least some of the computer code involved in performing the inventive methods of illustrative embodiments, such as health assessment code 200. For example, health assessment code 200 automatically assesses the health of a patient in an unbiased and objective manner in real time using natural language processing and machine learning.

In addition to health assessment code 200, computing environment 100 includes, for example, computer 101, wide area network (WAN) 102, end user device (EUD) 103, remote server 104, public cloud 105, and private cloud 106.

In this embodiment, computer 101 includes processor set 110 (including processing circuitry 120 and cache 121), communication fabric 111, volatile memory 112, persistent storage 113 (including operating system 122 and health assessment code 200, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

Computer 101 may take the form of a desktop computer, laptop computer, tablet computer, mainframe computer, quantum computer, or any other form of computer now known or to be developed in the future that is capable of, for example, running a program, accessing a network, and querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

Processor set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods of illustrative embodiments may be stored in health assessment code 200 in persistent storage 113.

Communication fabric 111 is the signal conduction path that allows the various components of computer 101 to communicate with each other. Typically, this fabric is made of switches and electrically conductive paths, such as the switches and electrically conductive paths that make up buses, bridges, physical input/output ports, and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

Persistent storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data, and re-writing of data. Some familiar forms of persistent storage include magnetic disks and solid-state storage devices. Operating system 122 may take several forms, such as various known proprietary operating systems or open-source Portable Operating System Interface-type operating systems that employ a kernel. The health assessment code included in block 200 includes at least some of the computer code involved in performing the inventive methods of illustrative embodiments.

Peripheral device set 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks, and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

Network module 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers, and edge servers.

EUD 103 is any computer system that is used and controlled by an end user (for example, a user of the health assessment services provided by computer 101), and may take any of the forms discussed above in connection with computer 101. EUD 103 typically receives helpful and useful data from the operations of computer 101. For example, in a hypothetical case where computer 101 is designed to provide a health assessment of a patient to the end user (e.g., healthcare professional such as a doctor), this health assessment would typically be communicated from network module 115 of computer 101 through WAN 102 to EUD 103. In this way, EUD 103 can display, or otherwise present, the health assessment of the patient to the end user. In some embodiments, EUD 103 may be a client device, such as thin client, heavy client, mainframe computer, desktop computer, laptop computer, tablet computer, smart watch, and so on.

Remote server 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a patient health assessment based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single entity. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

As used herein, when used with reference to items, "a set of" means one or more of the items. For example, a set of clouds is one or more different types of cloud environments. Similarly, "a number of," when used with reference to items, means one or more of the items. Moreover, "a group of" or "a plurality of" when used with reference to items, means two or more of the items.

Further, the term "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example may also include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

Health assessment has been performed the same way for over a century. That is, a trained healthcare professional (e.g., physician, clinician, therapist, or the like) examines and assesses a person with or without using some type of protocol. However, this approach is not scalable and is not consistent. For example, different healthcare professionals can arrive at different health assessments of the same person.

Illustrative embodiments provide unbiased and objective assessment of health conditions of humans, as compared to the traditional health assessment methods, based on crowdsourced knowledge of characteristics of specific health conditions using natural language processing and machine learning. As used herein, crowdsourcing involves obtaining specialized knowledge, ideas, or content by soliciting contributions from a network of targeted individuals, such as, for example, subject matter experts. Crowdsourced knowledge increases quality and reliability of health assessment of people. Thus, illustrative embodiments utilize this crowdsourced knowledge for improved health assessment of patients.

For example, illustrative embodiments incorporate knowledge from a plurality of subject matter experts (e.g., physicians, clinicians, therapists, and the like) into an objective metric to assess specific health conditions. Further, illustrative embodiments also incorporate into the objective metric knowledge extracted from clinically-used health assessment questionaries and/or literature for these different health conditions.

By illustrative embodiments aggregating the collected characteristics corresponding to a particular health condition from the plurality of subject matter experts (i.e., crowdsourced specialized knowledge) and the clinically-used health assessment questionaries and/or literature, illustrative embodiments are able to generate sentence embeddings corresponding to the characteristics of that particular health condition. In natural language processing, a sentence embedding is a representation of a sentence used in text analysis. Typically, the representation is a real-valued vector that encodes the meaning of the sentence in such a way that text that is closer in a predefined vector space are expected to be similar in meaning. In other words, words and sentences used in similar contexts are closer in the vector space. The vectors can be used to compute semantic similarity between 2 portions (e.g., words, phrases, sentences, or the like) of text. Sentence embeddings can be obtained using language modeling and feature learning techniques, where words, phrases, or sentences from a particular or general vocabulary domain are mapped to vectors of real numbers. Methods to generate this mapping include machine learning models, such as, for example, neural networks. Similar to word embeddings, a machine learning language model, such as, for example, a universal sentence encoder, bidirectional encoder representations from transformers, or the like, can generate sentence embeddings that convert a string of text into semantically-meaningful fixed-length vector representations.

Illustrative embodiments compare sentence embeddings corresponding to utterances made by a patient to the generated sentence embeddings corresponding to the characteristics of that particular health condition. Thus, illustrative embodiments are capable of providing an objective health assessment of that patient, along with monitoring condition progression or regression, treatment efficacy, and the like. As a result, illustrative embodiments provide services that are similar to what a trained healthcare professional does when assessing a patient, but in an unbiased and objective manner.

For example, for each particular health condition (e.g., depression, schizophrenia, chronic pain, or the like), illustrative embodiments collect sentences that characterize that particular health condition from a targeted group of subject matter experts who possess specialized authoritative knowledge regarding that particular health condition. However, it should be noted that depression, schizophrenia, and chronic pain are intended as examples only and not as limitations on illustrative embodiments. For example, illustrative embodiments can collect sentences that characterize other types of health conditions, such as diabetes, hepatitis, colitis, heart disease, lung disease, multiple sclerosis, chronic fatigue syndrome, or the like, from respective groups of subject matter experts having specialized knowledge corresponding to each different health condition.

Illustrative embodiments request that the group of subject matter experts provide sentences that according to the subject matter experts are pathognomonic of that particular health condition. In other words, the subject matter experts are providing sentences that are expected to be said by patients having that particular health condition. Moreover, illustrative embodiments collect a set of clinically-used questionnaires corresponding to that particular health condition. Illustrative embodiments then generate a plurality of sentence embeddings based on the collected sentences that characterize that particular health condition from the group of subject matter experts and the set of clinically-used questionnaires corresponding to that particular health condition using, for example, a machine learning language model such as a universal sentence encoder, bidirectional encoder representations from transformers, or the like.

In addition, illustrative embodiments generate a set of sentence embeddings from a transcription of patient utterances in response to an open-ended question being presented to the patient. Open-ended questions are questions that require more than a short, fixed response. For example, open-ended questions try to avoid answers such as "Yes," "No." or the like. Open-ended questions attempt to make the person who is answering the question give a more detailed and elaborate response. Illustrative embodiments utilize, for example, natural language understanding, natural language processing, and the like to generate the transcription of the patient utterances. Illustrative embodiments can also utilize prosody, which is different for different health conditions. Prosody identifies expressiveness in speech. Prosody includes, for example, intonation, stress, tone, and rhythm of speech. In other words, prosody provides additional context and meaning to spoken words. Illustrative embodiments train the machine learning model on prosody. For example, illustrative embodiments train the machine learning model using a plurality of audio recordings of subject matter experts or specially-trained actors who are speaking as a typical patient, imitating speech associated with that particular health condition. Natural language understanding can analyze unstructured speech for phenomenological experiences and their relationship with aspects of clinical symptomatology.

Illustrative embodiments measure vector similarity between the plurality of sentence embeddings generated from the characteristics of that particular health condition provided by the group of subject matter experts and the set of clinically-used questionnaires and the set of sentence embeddings generated from the transcription of utterances made by the patient. Illustrative embodiments select a similarity function or semantic distance metric to link the sentence-based health condition indicators uttered by the patient to the characteristics of that particular health condition obtained from sentences provided by the subject matter experts and clinical questionnaires. A similarity function is a real-valued function that quantifies the similarity between two objects. Cosine similarity is a commonly used similarity function for real-valued vectors, used, for example, to score the similarity of text embeddings in a defined vector space. Cosine similarity is the cosine of the angle between the vectors. Thus, cosine similarity does not depend on the magnitude of the vectors, but on their angle. Illustrative embodiments utilize vector similarity to assess whether the patient has that particular health condition or not. However, it should be noted that cosine similarity is intended as an example only and not as a limitation on illustrative embodiments. In other words, illustrative embodiments may utilize any type of similarity function or semantic distance metric.

Illustrative embodiments then measure similarity between the plurality of sentence embeddings generated from the characteristics of that particular health condition and the set of sentence embeddings generated from the transcription of the utterances made by the patient based on the selected similarity function or semantic distance metric. Illustrative embodiments notify the ordering healthcare professional via, for example, email, text message, social media post, page, or the like, regarding the patient for follow up in response to the measured similarity between the plurality of sentence embeddings generated from the characteristics of that particular health condition and the set of sentence embeddings generated from the transcription of the utterances made by the patient in response to the presented open-ended question.

Thus, illustrative embodiments provide one or more technical solutions that overcome a technical problem with an inability of current methods to provide an unbiased and objective health condition assessment of a patient in real time. As a result, these one or more technical solutions provide a technical effect and practical application in the field of healthcare.

With reference now to FIG. 2, a diagram illustrating an example of a health assessment system is depicted in accordance with an illustrative embodiment. Health assessment system 201 may be implemented in a computing environment, such as computing environment 100 in FIG. 1. Health assessment system 201 is a system of hardware and software components for automatically assessing whether a patient has a particular health condition in an unbiased and objective manner in real time.

In this example, health assessment system 201 includes computer 202, client devices 204, remote database 206, client device 208, and client device 210. However, it should be noted that health assessment system 201 is intended as an example only and not as a limitation on illustrative embodiments. For example, health assessment system 201 can include any number of computers, client devices, remote databases, and other devices and components not shown.

Computer 202, remote database 206, and client device 208 may be, for example, computer 101, remote database 130, and EUD 103, respectively, in FIG. 1. Client devices 204 represent a plurality of client devices that correspond to subject matter experts 212. Subject matter experts 212 represent a targeted group of individuals who have specialized knowledge 214 regarding health condition 216. However, it should be noted that subject matter experts 212 can represent a plurality of different groups of subject matter experts, each different group having specialized knowledge regarding a different health condition.

Health condition 216 can represent any type of human health condition, such as, for example, a mental health condition, neurodegenerative condition, psychological condition, musculoskeletal condition, neurological condition, cardiovascular condition, respiratory condition, gastrointestinal condition, or the like. Remote database 206 can represent a plurality of remote databases containing clinical health assessment questionnaires 218. Clinical health assessment questionnaires 218 represents a set of clinically-used questionnaires that correspond to health condition 216. However, it should be noted that clinical health assessment questionnaires 218 can represent a plurality of different types of clinical health assessment questionnaires 218 corresponding to a plurality of different types of health conditions.

Computer 202 requests that subject matter experts 212 provide sentences 220 that include characteristics 222 of health condition 216 based on specialized knowledge 214 of subject matter experts 212. Characteristics 222 are distinctive traits, qualities, or attributes that are pathognomonic of health condition 216. Subject matter experts 212 send sentences 220 to computer 202 using client devices 204. In addition, computer 202 retrieves clinical health assessment questionnaires 218, which correspond to health condition 216, from remote database 206. In response to retrieving clinical health assessment questionnaires 218, computer 202 extracts sentences from clinical health assessment questionnaires 218 that contain characteristics 222 of health condition 216.

In response to receiving sentences 220 from subject matter experts 212 and extracting sentences from clinical health assessment questionnaires 218, computer 202 generates characteristics sentence embeddings 224 using, for example, natural language processing. Characteristics sentence embeddings 224 represent a plurality of sentence embeddings corresponding to characteristics 222 of health condition 216.

Subsequently, ordering healthcare professional 226, sends health assessment request 228 associated with patient 230 to computer 202 using client device 208. In response to receiving health assessment request 228, computer 202 presents open-ended question 232, which is selected from one of clinical health assessment questionnaires 218 corresponding to health condition 216, to patient 230 via client device 210. In response to open-ended question 232, patient 230 sends utterance 234 to computer 202 using client device 210.

In response to receiving utterance 234, computer 202 generates utterance transcription 236 using, for example, natural language understanding. However, it should be noted that computer 202 can present a plurality of open-ended questions to patient 230 and receive a plurality of utterances from patient 230 in response. After generating utterance transcriptions for received utterances to the presented open-ended questions, computer 202 generates utterance sentence embeddings 238 from the transcription of utterances using, for example, natural language processing. Utterance sentence embeddings 238 represent a set of sentence embeddings corresponding to the utterances of patient 230.

Computer 202 measures similarity between characteristics sentence embeddings 224 and utterance sentence embeddings 238 using similarity function 240 to determine whether patient 230 has health condition 216 or not. Similarity function 240 can be, for example, cosine similarity. Computer 202 sends health assessment result 242 to ordering healthcare professional 226 based on the measured similarity between characteristics sentence embeddings 224 and utterance sentence embeddings 238.

Figure 3:
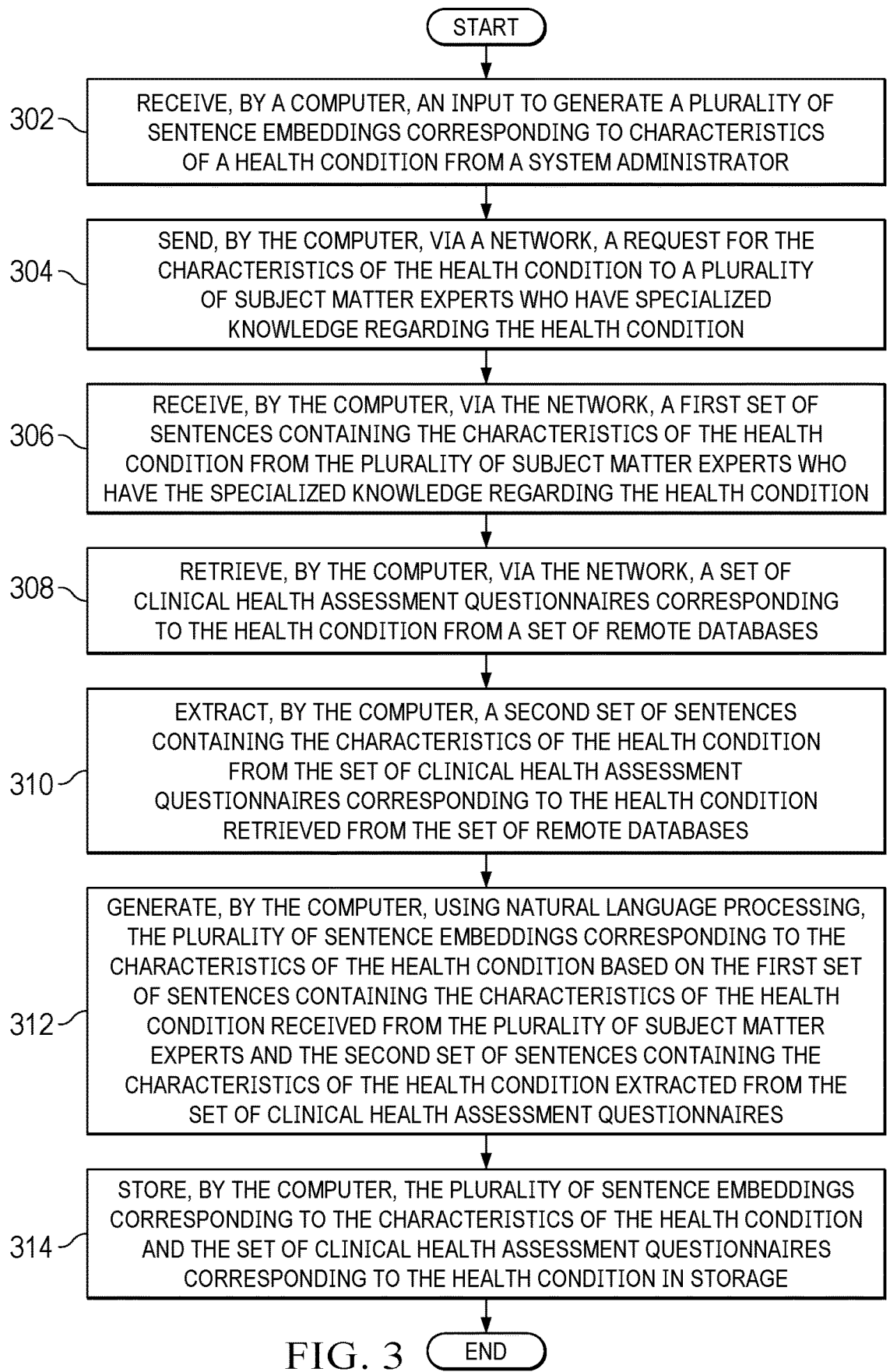
FIG. 3 is a flowchart illustrating a process for generating sentence embeddings corresponding to characteristics of a health condition in accordance with an illustrative embodiment.

With reference now to FIG. 3, a flowchart illustrating a process for generating sentence embeddings corresponding to characteristics of a health condition is shown in accordance with an illustrative embodiment. The process shown in FIG. 3 may be implemented in a computer, such as, for example, computer 101 in FIG. 1 or computer 202 in FIG. 2. For example, the process shown in FIG. 3 may be implemented in health assessment code 200 in FIG. 1.

The process begins when the computer receives an input to generate a plurality of sentence embeddings corresponding to characteristics of a health condition from a system administrator (step 302). In response to receiving the input, the computer, via a network, sends a request for the characteristics of the health condition to a plurality of subject matter experts who have specialized knowledge regarding the health condition (step 304).

Subsequently, the computer, via the network, receives a first set of sentences containing the characteristics of the health condition from the plurality of subject matter experts who have the specialized knowledge regarding the health condition (step 306). In addition, the computer, via the network, retrieves a set of clinical health assessment questionnaires corresponding to the health condition from a set of remote databases (step 308). The computer extracts a second set of sentences containing the characteristics of the health condition from the set of clinical health assessment questionnaires corresponding to the health condition retrieved from the set of remote databases (step 310).

Afterward, the computer, using natural language processing, generates the plurality of sentence embeddings corresponding to the characteristics of the health condition based on the first set of sentences containing the characteristics of the health condition received from the plurality of subject matter experts and the second set of sentences containing the characteristics of the health condition extracted from the set of clinical health assessment questionnaires (step 312). The computer stores the plurality of sentence embeddings corresponding to the characteristics of the health condition and the set of clinical health assessment questionnaires corresponding to the health condition in storage (step 314). Thereafter, the process terminates.

Figure 4B:
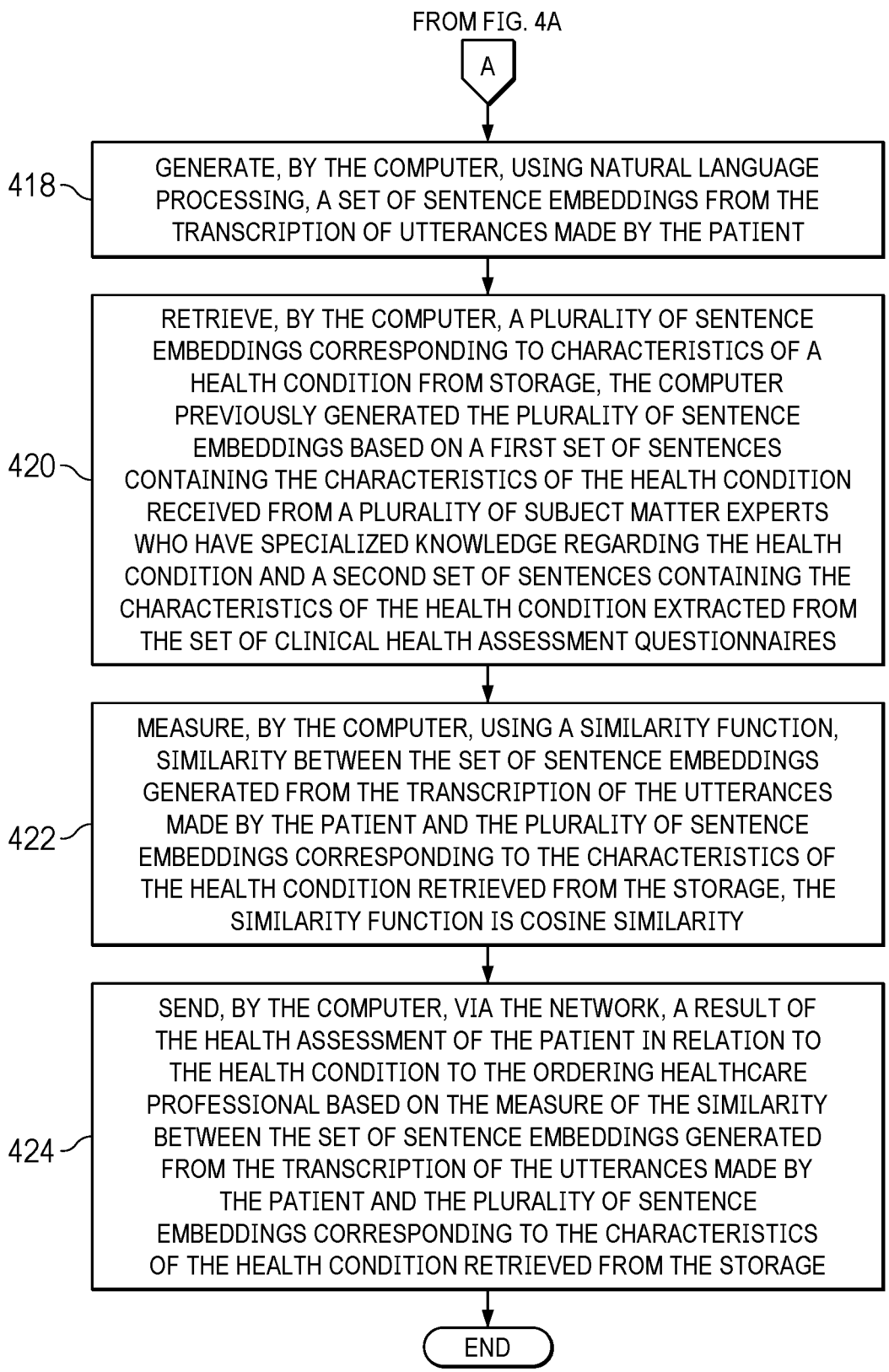

With reference now to FIGS. 4A-4B, a flowchart illustrating a process for objectively assessing patient health is shown in accordance with an illustrative embodiment. The process shown in FIGS. 4A-4B may be implemented in a computer, such as, for example, computer 101 in FIG. 1 or computer 202 in FIG. 2. For example, the process shown in FIGS. 4A-4B may be implemented in health assessment code 200 in FIG. 1.

The process begins when the computer, via a network, receives a request to perform a health assessment of a patient from an ordering healthcare professional (step 402). The computer provides a health assessment service. The request provides patient-authorized contact information corresponding to the patient.

The computer, via the network, establishes a connection with a client device of the patient to perform the health assessment of the patient using the patient-authorized contact information corresponding to the patient (step 404). The client device of the patient is one of a landline phone, cellular phone, smart phone, personal computer, laptop computer, tablet computer, or smart television. In addition, the computer retrieves a set of open-ended questions from storage to perform the health assessment of the patient (step 406). Further, the computer selects an open-ended question from the set of open-ended questions (step 408). The computer, via the network, presents the open-ended question to the patient (step 410). The computer presents the question using one of a display or a speaker of the client device corresponding to the patient.

Subsequently, the computer, via the network, receives an utterance of the patient in response to the open-ended question being presented to the patient (step 412). However, it should be noted that in addition to, or instead of, receiving the utterance, the computer can receive text from the patient in response to the open-ended question. The computer, using natural language understanding, generates a transcription of the utterance of the patient responding to the open-ended question (step 414).

Afterward, the computer makes a determination as to whether another open-ended question exists in the set of clinical health assessment questionnaires (step 416). If the computer determines that another open-ended question does exist in the set of clinical health assessment questionnaires, yes output of step 416, then the process returns to step 408 where the computer selects another open-ended question to present to the patient. If the computer determines that another open-ended question does not exist in the set of clinical health assessment questionnaires, no output of step 416, then the computer, using natural language processing, generates a set of sentence embeddings from the transcription of utterances made by the patient (step 418).

Further, the computer retrieves a plurality of sentence embeddings corresponding to characteristics of a health condition from storage (step 420). The computer previously generated the plurality of sentence embeddings based on a first set of sentences containing the characteristics of the health condition received from a plurality of subject matter experts who have specialized knowledge regarding the health condition and a second set of sentences containing the characteristics of the health condition extracted from the set of clinical health assessment questionnaires corresponding to the health condition. The computer, using a similarity function, measures similarity between the set of sentence embeddings generated from the transcription of the utterances made by the patient and the plurality of sentence embeddings corresponding to the characteristics of the health condition retrieved from the storage (step 422). The similarity function is, for example, cosine similarity.

The computer, via the network, sends a result of the health assessment of the patient in relation to the health condition to the ordering healthcare professional based on the measure of the similarity between the set of sentence embeddings generated from the transcription of the utterances made by the patient and the plurality of sentence embeddings corresponding to the characteristics of the health condition retrieved from the storage (step 424). Thereafter, the process terminates.

Thus, illustrative embodiments of the present disclosure provide a computer-implemented method, computer system, and computer program product for automatically assessing health of a patient in an unbiased and objective manner in real time. The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for objective health assessment, the computer-implemented method comprising:
training, by a computer, a machine learning model (MLM) utilizing a plurality of audio recordings received from a plurality of subject matter experts or specially trained actors speaking as a typical patient with a health condition wherein the plurality of audio recordings include a first set of sentences containing a first set of characteristics of the health condition that are pathognomic of the health condition and associates prosody related to the health condition;
retrieving, by the computer, a set of clinical health assessment questionnaires corresponding to the health condition from a set of remote databases;
extracting, by the computer, a second set of sentences containing a second set of characteristics of the health condition from the set of clinical health assessment questionnaires;
generating, by the computer using natural language processing, a plurality of sentence embeddings corresponding to a combined set of characteristics of the health condition based on the first set of sentences and the second set of sentences, wherein the plurality of sentence embeddings are real-valued vectors that encode meaning of the sentences in a vector space;
storing the combined set of characteristics of the health condition and the plurality of sentence embeddings in a storage device;
establishing, by the computer, a connection with a client device of a patient using patient-authorized contact information to perform a health assessment of the patient;
retrieving, by the computer, a set of open-ended questions from the set of clinical health assessment questionnaires corresponding to the health condition;
presenting, by the computer via a display or a speaker of the client device, an open-ended question from the set of open-ended questions to the patient;
receiving, by the computer via the client device, an utterance of the patient in response to the open-ended question being presented to the patient;
generating, by the computer, using natural language understanding a transcription of the utterance of the patient responding to the open-ended question;
generating, by the computer using the trained MLM, a set of sentence embeddings from the transcription of the utterance made by the patient;
retrieving, by the computer, the plurality of sentence embeddings corresponding to the combined set of characteristics of a health condition from the storage device;
measuring, by the computer, similarity between the set of sentence embeddings generated from the transcription of the utterance made by the patient and the plurality of sentence embeddings corresponding to the combined set of characteristics of the health condition stored in the storage device
and their relationship with aspects of clinical symptomatology of the health condition to determine results of a health assessment of the patient; and
sending, by the computer, via a network to a client device of healthcare professional the results of the health assessment of the patient based on the similarity between the set of sentence embeddings generated from the transcription of the utterance made by the patient and the plurality of sentence embeddings corresponding to the characteristics of the health condition.

2. The computer-implemented method of claim 1, further comprising:
receiving, by the computer, an input to generate the plurality of sentence embeddings corresponding to the combined set of characteristics of the health condition;
sending, by the computer, a request for the first set of characteristics of the health condition to the plurality of subject matter experts who have specialized knowledge regarding the health condition; and
receiving, by the computer, the first set of sentences containing the first set of characteristics of the health condition from the plurality of subject matter experts who have the specialized knowledge regarding the health condition.

3. The computer-implemented method of claim 1, further comprising:
retrieving, by the computer, a number of clinical health assessment questionnaires corresponding to the health condition, wherein the number is at least two; and
extracting, by the computer, a third set of sentences containing the characteristics of the health condition from the number of clinical health assessment questionnaires corresponding to the health condition.

4. The computer-implemented method of claim 1, further comprising:
retrieving, by the computer, a set of questions to perform the health assessment of the patient;
selecting, by the computer, the question from the set of questions; and
presenting, by the computer, the question to the patient.

5. The computer-implemented method of claim 1, wherein the characteristics are distinctive traits, qualities, or attributes that are pathognomonic of the health condition.

6. The computer-implemented method of claim 1, wherein the computer utilizes a similarity function to measure the similarity between the set of sentence embeddings generated from the transcription of the utterance made by the patient and the plurality of sentence embeddings corresponding to the characteristics of the health condition.

7. The computer-implemented method of claim 6, wherein the similarity function is cosine similarity.

8. The computer-implemented method of claim 1, further comprising:
training the MLM to utilize prosody by recognizing and identifying elements of expressiveness selected from a group consisting of intonation, stress, tone, and rhythm of speech.

9. The computer-implemented method of claim 1, further comprising:
sending the results of the health assessment of the patient to healthcare professional via an approach selected from a group consisting of email, text message, social media post, and page.

10. A computer system for objective health assessment, the computer system comprising:
a communication fabric;
a storage device connected to the communication fabric, wherein the storage device stores program instructions; and
a processor connected to the communication fabric, wherein the processor executes the program instructions to:
train a machine learning model (MLM) utilizing a plurality of audio recordings received from subject matter experts or specially trained actors speaking as a typical patient with a health condition wherein the plurality of audio recordings include a first set of sentences containing a first set of characteristics of the health condition that are pathognomic of the health condition and associates prosody related to the health condition;

retrieve a set of clinical health assessment questionnaires corresponding to the health condition from a set of remote databases;

extract a second set of sentences containing a second set of characteristics of the health condition from the set of clinical health assessment questionnaires;

generate using natural language processing, a plurality of sentence embeddings corresponding to a combined set of characteristics of the health condition based on the first set of sentences and the second set of sentences, wherein the plurality of sentence embeddings are real-valued vectors that encode meaning of the sentences in a vector space;

store the combined set of characteristics of the health condition and the plurality of sentence embeddings in a storage device;

establish a connection with a client device of a patient using patient-authorized contact information to perform a health assessment of the patient;

retrieve a set of open-ended questions from the set of clinical health assessment questionnaires corresponding to the health condition;

present via a display or a speaker of the client device, an open-ended question from the set of open-ended questions to the patient;

receive via the client device an utterance of the patient in response to the open-ended question being presented to the patient;

generate using natural language understanding a transcription of the utterance of the patient responding to the open-ended question;

generate using the trained MLM a set of sentence embeddings from the transcription of the utterance made by the patient;

retrieve the plurality of sentence embeddings corresponding to the combined set of characteristics of the health condition from the storage device;

measure similarity between the set of sentence embeddings generated from the transcription of the utterance made by the patient and the plurality of sentence embeddings corresponding to the combined set of characteristics of the health condition stored in the storage device and their relationship with aspects of clinical symptomatology of the health condition to determine results of a health assessment of the patient; and send via a network to a client device of healthcare professional the results of the health assessment of the patient based on the similarity between the set of sentence embeddings generated from the transcription of the utterance made by the patient and the plurality of sentence embeddings corresponding to the characteristics of the health condition.

11. The computer system of claim 10, wherein the processor further executes the program instructions to:

receive an input to generate the plurality of sentence embeddings corresponding to the combined set of characteristics of the health condition;

send a request for the first set of characteristics of the health condition to the plurality of subject matter experts who have specialized knowledge regarding the health condition; and receive the first set of sentences containing the first set of characteristics of the health condition from the plurality of subject matter experts who have the specialized knowledge regarding the health condition.

12. The computer system of claim 10, wherein the processor further executes the program instructions to:

retrieve a number of clinical health assessment questionnaires corresponding to the health condition, wherein the number is at least two; and extract a third set of sentences containing the characteristics of the health condition from the number of clinical health assessment questionnaires corresponding to the health condition.

13. The computer system of claim 10, wherein the processor further executes the program instructions to:

train the MLM to utilize prosody by recognizing and identifying elements of expressiveness selected from a group consisting of intonation, stress, tone, and rhythm of speech.

14. The computer system of claim 10, wherein the processor further executes the program instructions to:

send the results of the health assessment of the patient to healthcare professional via an approach selected from a group consisting of email, text message, social media post, and page.

15. A computer program product for objective health assessment, the computer program product comprising a non-transitory computer-readable storage medium having program instructions embodied therewith, the program instructions executable by a computer to cause the computer to:

train, a machine learning model (MLM) utilizing a plurality of audio recordings received from subject matter experts or specially trained actors speaking as a typical patient with a health condition wherein the plurality of audio recordings include a first set of sentences containing a first set of characteristics of the health condition that are pathognomic of the health condition and associates prosody related to the health condition;

retrieve a set of clinical health assessment questionnaires corresponding to the health condition from a set of remote databases;

extract a second set of sentences containing a second set of characteristics of the health condition from the set of clinical health assessment questionnaires;

generate using natural language processing, a plurality of sentence embeddings corresponding to a combined set of characteristics of the health condition based on the first set of sentences and the second set of sentences, wherein the plurality of sentence embeddings are real-valued vectors that encode meaning of the sentences in a vector space;

store the combined set of characteristics of the health condition and the plurality of sentence embeddings in a storage device;

establish a connection with a client device of a patient using patient-authorized contact information to perform a health assessment of the patient;

retrieve a set of open-ended questions from the set of clinical health assessment questionnaires corresponding to the health condition;

present via a display or a speaker of the client device, an open-ended question from the set of open-ended questions to the patient;

receive via the client device an utterance of the patient in response to the open-ended question being presented to the patient;

generate using natural language understanding a transcription of the utterance of the patient responding to the open-ended question;
generate using the trained MLM a set of sentence embeddings from the transcription of the utterance made by the patient;
retrieve the plurality of sentence embeddings corresponding to the combined set of characteristics of a health condition from the storage device;
measure similarity between the set of sentence embeddings generated from the transcription of the utterance made by the patient and the plurality of sentence embeddings corresponding to the combined set of characteristics of the health condition stored in the storage device
and their relationship with aspects of clinical symptomatology of the health condition to determine results of a health assessment of the patient; and
send via a network to a client device of healthcare professional the results of the health assessment of the patient based on the similarity between the set of sentence embeddings generated from the transcription of the utterance made by the patient and the plurality of sentence embeddings corresponding to the characteristics of the health condition.

16. The computer program product of claim 15, wherein the program instructions further cause the computer to:
receive an input to generate the plurality of sentence embeddings corresponding to the combined set of characteristics of the health condition;
send a request for the first set of characteristics of the health condition to the plurality of subject matter experts who have specialized knowledge regarding the health condition; and
receive the first set of sentences containing the first set of characteristics of the health condition from the plurality of subject matter experts who have the specialized knowledge regarding the health condition.

17. The computer program product of claim 15, wherein the program instructions further cause the computer to:
retrieve a number of clinical health assessment questionnaires corresponding to the health condition, wherein the number is at least two; and
extract a third set of sentences containing the characteristics of the health condition from the number of clinical health assessment questionnaires corresponding to the health condition.

18. The computer program product of claim 15, wherein the program instructions further cause the computer to:
retrieve a set of questions to perform the health assessment of the patient;
select the question from the set of questions; and
present the question to the patient.

19. The computer program product of claim 15, wherein the program instructions further cause the computer to:
train the MLM to utilize prosody by recognizing and identifying elements of expressiveness selected from a group consisting of intonation, stress, tone, and rhythm of speech.

20. The computer program product of claim 15, wherein the program instructions further cause the computer to:
send the results of the health assessment of the patient to healthcare professional via an approach selected from a group consisting of email, text message, social media post, and page.

* * * * *